US008618108B2

(12) United States Patent
King et al.

(10) Patent No.: US 8,618,108 B2
(45) Date of Patent: *Dec. 31, 2013

(54) METHODS OF MAKING CYCLIC, N-AMINO FUNCTIONAL TRIAMINES

(75) Inventors: Stephen W. King, League City, TX (US); Stefan K. Mierau, South Charleston, WV (US); Thomas Z. Srnak, Arlington Heights, IL (US)

(73) Assignee: Union Carbide Chemicals & Plastics Technology LLC, Midland, MI (US)

( * ) Notice: Subject to any disclaimer, the term of this patent is extended or adjusted under 35 U.S.C. 154(b) by 435 days.

This patent is subject to a terminal disclaimer.

(21) Appl. No.: 12/587,338

(22) Filed: Oct. 6, 2009

(65) Prior Publication Data

US 2010/0094007 A1    Apr. 15, 2010

Related U.S. Application Data

(60) Provisional application No. 61/195,412, filed on Oct. 6, 2008.

(51) Int. Cl.
*A61K 31/50* (2006.01)
*A61K 31/501* (2006.01)
*A61K 31/497* (2006.01)
*C07D 241/04* (2006.01)
*C07D 295/00* (2006.01)

(52) U.S. Cl.
USPC .................. 514/252.12; 544/401; 544/402

(58) Field of Classification Search
USPC ........................... 514/252.12; 544/401, 402
See application file for complete search history.

(56) References Cited

U.S. PATENT DOCUMENTS

| | | | |
|---|---|---|---|
| 2,861,995 A | 11/1958 | MacKenzie | |
| 3,110,732 A | 11/1963 | Speranza et al. | |
| 3,394,186 A | 7/1968 | Muhlbauer | |
| 3,658,692 A | 4/1972 | Gilbert et al. | |
| 3,847,754 A | 11/1974 | Oliver | |
| 4,032,411 A | 6/1977 | Tornquist et al. | |
| 4,073,750 A | 2/1978 | Yates et al. | |
| 4,111,840 A | 9/1978 | Best | |
| 4,123,462 A | 10/1978 | Best | |
| 4,209,424 A | 6/1980 | Le Goff et al. | |
| 4,264,776 A | 4/1981 | Hershman et al. | |
| 4,328,370 A | 5/1982 | Fazio | |
| 4,400,539 A | 8/1983 | Gibson et al. | |
| 4,404,405 A | 9/1983 | Winters | |
| 4,510,263 A | 4/1985 | Pereira et al. | |
| 4,552,961 A | 11/1985 | Herdle | |
| 4,568,746 A | 2/1986 | Cowherd, III | |
| 4,584,405 A | 4/1986 | Vanderpool | |
| 4,602,091 A | 7/1986 | Brennan | |
| 4,708,945 A | 11/1987 | Murrell et al. | |
| 4,729,981 A | 3/1988 | Kobylinski et al. | |
| 4,801,573 A | 1/1989 | Eri et al. | |
| 4,806,517 A | 2/1989 | Vanderpool et al. | |
| 4,845,296 A | 7/1989 | Ahmed et al. | |
| 4,870,044 A | 9/1989 | Kukes et al. | |
| 4,883,826 A | 11/1989 | Marugg et al. | |
| 4,888,316 A | 12/1989 | Gardner et al. | |
| 4,906,782 A | 3/1990 | Hara et al. | |
| 4,922,024 A | 5/1990 | Bowman et al. | |
| 4,927,931 A | 5/1990 | Molzahn et al. | |
| 4,983,735 A | 1/1991 | Hartwell et al. | |
| 5,030,740 A | 7/1991 | Bowman et al. | |
| 5,073,635 A | 12/1991 | Bowman et al. | |
| 5,120,815 A | 6/1992 | Marugg et al. | |
| 5,166,442 A | 11/1992 | Hartwell et al. | |
| 5,210,306 A | 5/1993 | Doumaux, Jr. et al. | |
| 5,214,215 A | 5/1993 | King et al. | |
| 5,225,599 A | 7/1993 | King et al. | |
| 5,225,600 A | 7/1993 | King et al. | |
| 5,248,827 A | 9/1993 | Hara et al. | |
| 5,256,786 A | 10/1993 | Bowman et al. | |
| 5,288,909 A | 2/1994 | Hartwell et al. | |
| 5,321,160 A | 6/1994 | Hironaka et al. | |
| 5,352,835 A | 10/1994 | Dai et al. | |

(Continued)

FOREIGN PATENT DOCUMENTS

| | | |
|---|---|---|
| EP | 0163253 | 12/1985 |
| EP | 0197611 | 10/1986 |

(Continued)

OTHER PUBLICATIONS

Richle, Reactions of Aliphatic α-ω-Diamines in H+-Pentasils, J. of Catalysis 144, 556-568 (1993).*
PCT Written Opinion of the International Searching Authority for International Application No. PCT/US2009/005471, pp. 1-8.
Abstract, Kiebach and Ragnar et al., "Solvothermal synthesis of [C6H17N3]Sb10S16: A new thioantimonate(III) with an in-situ formed organic amine cation", Database Caplus [Online], Chemical Abstracts Service, Columbus, Ohio, pp. 1314-1319 (2004).
Komiyama et al., "Concentration Profiles in Impregnation of Porous Catalysts: Nickel on Alumina," Journal of Catalysis, vol. 63, School of Chemical Engineering, Cornell University, and Chevron Research Company, pp. 35-52 (1979).

(Continued)

*Primary Examiner* — Erich A Leeser
(74) *Attorney, Agent, or Firm* — Kagen Binder, PLLC (57) ABSTRACT

The present invention provides strategies for making cyclic triamines. Reactant media including certain precursors and/or certain types of catalysts can be converted into cyclic triamines with improved conversion and selectivity. The strategies can be incorporated into reactions that involve transamination schemes and/or reductive amination schemes. In the case of transamination, for instance, using transamination to cause ring closure of higher amines in the presence of a suitable catalyst leads to desired cyclic triamines with notable conversion and yield. In the case of reductive amination, reacting suitable polyfunctional precursors in the presence of a suitable catalyst also yields cyclic triamines via ring closure with notable selectivity and conversion. Both transamination and reductive amination methodologies can be practiced under much milder temperatures than are used when solely acid catalysts are used. Preferred embodiments can produce reaction mixtures that are generally free of salt by-products.

5 Claims, 4 Drawing Sheets

(56) References Cited

U.S. PATENT DOCUMENTS

| | | |
|---|---|---|
| 5,362,914 A | 11/1994 | Su |
| 5,410,086 A | 4/1995 | Burgess |
| 5,410,087 A | 4/1995 | Hartwell |
| H1447 H | 6/1995 | Linton |
| 5,455,352 A | 10/1995 | Huellmann et al. |
| 5,552,363 A | 9/1996 | Pannell et al. |
| 5,554,792 A | 9/1996 | Sawayama et al. |
| 5,567,847 A | 10/1996 | Vedage et al. |
| 5,721,305 A | 2/1998 | Eshuis et al. |
| 5,750,790 A | 5/1998 | King |
| 5,817,593 A | 10/1998 | Chang et al. |
| 5,851,948 A | 12/1998 | Chuang et al. |
| 5,935,889 A | 8/1999 | Murrell et al. |
| 6,117,814 A | 9/2000 | Plecha et al. |
| 6,124,367 A | 9/2000 | Plecha et al. |
| 6,169,207 B1 | 1/2001 | Tsuneki et al. |
| 6,222,008 B1 | 4/2001 | Gelles |
| 6,235,677 B1 | 5/2001 | Manzer et al. |
| 6,306,795 B1 | 10/2001 | Ryan et al. |
| 6,465,530 B2 | 10/2002 | Roy-Auberger et al. |
| 6,469,214 B2 | 10/2002 | Melder et al. |
| 6,534,441 B1 | 3/2003 | Bartley et al. |
| 6,576,796 B1 | 6/2003 | Funk et al. |
| 6,703,343 B2 | 3/2004 | Park |
| 6,977,273 B2 | 12/2005 | Roy-Auberger et al. |
| 7,045,485 B2 | 5/2006 | Kelkar et al. |
| 7,053,246 B2 | 5/2006 | Gerlach et al. |
| 7,053,247 B2 | 5/2006 | Lif et al. |
| 7,056,857 B2 | 6/2006 | Srinivasan et al. |
| 7,067,455 B2 | 6/2006 | Chen et al. |
| 7,256,154 B2 | 8/2007 | Moon et al. |
| 7,323,100 B2 | 1/2008 | Espinoza et al. |
| 7,341,976 B2 | 3/2008 | Espinoza et al. |
| 7,348,293 B2 | 3/2008 | Timken |
| 7,393,978 B2 | 7/2008 | Frauenkron et al. |
| 7,541,310 B2 | 6/2009 | Espinoza et al. |
| 7,595,276 B2 | 9/2009 | Kodama et al. |
| 7,745,369 B2 | 6/2010 | Bhan et al. |
| 7,824,656 B2 | 11/2010 | Idem et al. |
| 7,981,836 B2 | 7/2011 | Kanazirev |
| 2003/0013873 A1 | 1/2003 | Neumann et al. |
| 2005/0095189 A1 | 5/2005 | Brey et al. |
| 2006/0030726 A1 | 2/2006 | Telschow |
| 2007/0100144 A1 | 5/2007 | Frauenkron et al. |
| 2008/0003131 A1 | 1/2008 | Bauer et al. |
| 2010/0056366 A1 | 3/2010 | Lee |
| 2010/0087685 A1 | 4/2010 | King et al. |
| 2010/0094008 A1* | 4/2010 | King et al. .................. 544/402 |
| 2012/0238780 A1 | 9/2012 | King et al. |
| 2012/0277435 A1 | 11/2012 | King et al. |
| 2013/0023698 A1 | 1/2013 | King et al. |

FOREIGN PATENT DOCUMENTS

| | | | |
|---|---|---|---|
| EP | 0197612 | 10/1986 | |
| EP | 0254335 | 1/1988 | |
| EP | 0284398 | 9/1988 | |
| EP | 0 526 851 A2 | 2/1993 | |
| EP | 0075940 | 9/1994 | |
| EP | 0737669 | 10/1996 | |
| EP | 1211238 | 6/2002 | |
| EP | 1249440 | 10/2002 | |
| GB | 1508460 | 4/1978 | |
| IL | 57019 | 9/1983 | |
| JP | 0509777 | 4/1993 | |
| RU | 2186761 | 8/2002 | |
| RU | 2226188 | 3/2004 | |
| RU | 2226189 | 3/2004 | |
| WO | WO 99/24389 | 5/1999 | |
| WO | WO 01/44150 | 6/2001 | |
| WO | WO 01/66247 | 9/2001 | |
| WO | WO 01/98243 | 12/2001 | |
| WO | WO 03/010125 | 2/2003 | |
| WO | WO 2005/012223 | 2/2005 | |
| WO | WO 2005/014523 | 2/2005 | |
| WO | WO 2005/061430 | 7/2005 | |
| WO | WO 2006/053342 | 5/2006 | |
| WO | WO 2006/060206 | 6/2006 | |
| WO | WO 2006/114417 | 11/2006 | |
| WO | WO 2007/093514 | 8/2007 | |
| WO | 2008104582 | 9/2008 | |
| WO | WO 2008/104582 | * 9/2008 | .......... C07D 211/14 |
| WO | WO 2009/083580 | 7/2009 | |

OTHER PUBLICATIONS

Lewi, Abstract, Database Beilstein (online), Beilstein Institute for Organic Chemistry, Doklady Akademii Nauk SSSR, vol. 78, pp. 725-727 (1951).

Tanabe et al., "A New Hypothesis Regarding the Surface Acidity of Binary Metal Oxides," Bulletin of the Chemical Society of Japan, vol. 47(5), Department of Chemistry, Faculty of Science, Hokkaido University, pp. 1064-1066 (1974).

Reichle, Walter T., "Reactions of Aliphatic Diamines in H+-Pentasils," Journal of Catalysis 144, pp. 556-568, Jun. 3, 1993.

Zagidullin, R.N., Abstract, "Simultaneous manufacture of acyclic and cyclic di- and polyethylenepolyamines", pp. 267-269, 1987.

Zagidullin, R.N., Abstract, "Method of Synthesis of Diethylenetriamine," p. 1, Aug. 10, 2002.

Zagudullin, R.N., Abstract, "Method of Producing Di- and Polyamines," p. 1, Mar. 27, 2004.

Olson, "Thermodynamics of hydrogen-bonding mixtures 4: $G^E$, $H^E$, $S^E$ and $C^E_p$ and possible double azeotropy of water + N-methylethylenediamine," Fluid Phase Equilibria 185 (2001) pp. 209-218.

* cited by examiner

Nitrilotriacetonitrile

Fig. 12 unsym DiHEED

N,N-Bis(2-hydroxyethyl)ethylenediamine

Fig. 13 sym DiHEED
N,N'-Bis(2-hydroxyethyl)ethylenediamine

Fig. 14

2-[Bis(2-Aminoethyl)Amino]Ethanol

Fig. 15

HEDETA 2-(2-(2-Aminoethylamino)Ethylamino)Ethanol

Fig. 16

HEP

Fig. 17

TEA

METHODS OF MAKING CYCLIC, N-AMINO FUNCTIONAL TRIAMINES

PRIORITY

The present non-provisional patent Application claims benefit from U.S. Provisional Patent Application Ser. No. 61/195,412, filed on Oct. 6, 2008, by Stephen W. King, and titled METHODS OF MAKING CYCLIC, N-AMINO FUNCTIONAL TRIAMINES, wherein the entirety of said provisional patent application is incorporated herein by reference.

FIELD OF THE INVENTION

The present invention relates to processes for making cyclic triamines using transamination and/or reductive amination techniques. In the case of transamination, the cyclic-triamines are made from higher amine precursors via ring closure reactions in the presence of a suitable catalyst. In the case of reductive amination, the cyclic triamines are made in the presence of a suitable catalyst from desirable polyfunctional precursors comprising at least one amine and at least one other kind of functionality such as hydroxyl, nitrile, additional amine, and the like.

BACKGROUND OF THE INVENTION

Cyclic triamines such as aminoethylpiperazine ("AEP") have many industrial uses. For instance, these compounds are useful as dispersants, epoxy curing agents, chelants, catalysts, accelerators, hardeners, extenders in polymer fabrication, starting materials in the preparation of other amines, starting materials for making pesticides, and the like. AEP is also known by other names including 2-piperazin-1-ylethaneamine; 2-(1-piperazinyl)ethylamine; N-AEP, N-(2-aminoethyl) piperazine; 2-piperazinoethylamine; 1-(2-aminoethyl) piperazine, 1-piperazine ethaneamine, and 1-aminoethylpiperazine.

A variety of processes for making cyclic triamines are known. According to one approach, AEP is a by-product formed from the reaction of ethylenedichloride (EDC) and ammonia or amines to form higher amines. See, e.g., Russian Patent Documents 2226188 and 2186761 and also *Khimicheskaya Promyshlennost* (Moscow, Russian Federation) (1987), (5) 267-9. However, in these reactions, the amount of AEP produced generally is small relative to the entire product mix. Also, undue amounts of salts can also result. Excessive salt production can complicate purification and/or disposal.

Cyclic triamines can also be formed by reacting hydroxyl functional reactants (e.g., monoethanolamine or ethylene glycol) and/or amines with other amines or ammonia in the presence of acid catalysts at high temperatures, e.g., 300° C. or higher. Acid catalysts include, for example, phosphorous doped, niobium doped, or tungsten doped metal oxides and several mixed metal oxides including zeolites. For example, U.S. Pat. No. 5,256,786 uses a magnesium silicate catalyst with piperazine (PIP) and ethylenediamine (EDA) as feed to produce AEP at 53% selectivity at 9% conversion. U.S. Pat. No. 5,073,635 shows examples of monoethanolamine (MEA) and PIP (1/1 mole ratio) with other metal silicates (Y, La, Ce, Nb, Zr, Ti) with conversions of ~20-40% and AEP selectivities of 70-84%.

U.S. Pat. No. 4,983,735 claims heteropolytungstates for the MEA+PIP reaction. Fixed bed results show up to 68% conversion of PIP with about 65% selectivity to aminoethylpiperazine (AEP).

U.S. Pat. No. 5,030,740 teaches the use of tungsten oxide/titania for conversion of crude piperazine and MEA to AEP. Here selectivity to AEP is lower in part due to the high MEA/PIP ratio of 1:3, the relatively high conversion of MEA, and the reaction of EDA and diethylenetriamine (DETA) with MEA.

U.S. Pat. No. 4,927,931 has examples based on niobium oxide and niobium phosphate catalysts. Selectivity is lower than with the silicates.

Journal of Catalysis, 144(2), 556-68; 1993 discloses using a H+-pentasil zeolite (Si/Al=25-19,000) at 350 C, a LHSV approximately 0.8 h-1, atm. pressure in a plug flow reactor. Ethylenediamine and its linear and cyclic oligomers result in piperazine and 1,4-diabicyclo(2.2.2)octane (TEDA), with small levels of AEP being formed.

U.S. Pat. No. 5,225,599 discloses a process for the preparation of triethylenetetramine and N-(2-aminoethyl)ethanolamine. This process comprises the condensation of an alkyleneamine and an alkylene glycol in the presence of a condensation catalyst selected from Group IVB oxides or Group VIB compounds and a catalyst promoter. A mixture of silicotungstic acid (18 g), $H_2O$, and $TiO_2/WO_3$ (55 g) was heated to 350 to give a catalyst. A mixture of ethylenediamine and ethylene glycol (2.95 mol ratio) was fed into a tube containing the above catalyst at 269.8 and 614.7 psig to give a product containing 6.13% by weight piperazine, 18.71% by weight triethylenetetramine, 47.84% by weight N-(2-aminethyl)ethanolamine; and 2.39% by weight N-(2-aminoethyl) piperazine, and 24.93% by weight other products.

U.S. Pat. No. 4,906,782 discloses a process whereby alkyleneamines having an increased number of alkylene units are prepared by reacting $NH_3$ and/or an alkyleneamine with an alkanolamine in the presence of a Nb-containing catalyst insoluble or slightly soluble in the aqueous reaction solution. Ethylenediamine 90, monoethanolamine 45, and $NbO_5$ 1.4 g were heated at 300 for 5 to give piperazine 2.3, diethylenetriamine 59.8, N-(2-aminoethyl)ethanolamine 2.6, —N-(2-aminoethyl)piperazine 1.0, triethylenetetramine (isomers) 15.0, tetraethylenepentamine (isomers) 2.0, and pentaethylenehexamine (isomers) 1.0%, vs: 0.1, 76.0, 23.8, 0, 0, 0, 0, respectively, when using silica-alumina in place of $NbO_5$.

In U.S. Pat. No. 4,922,024 amines (esp. acyclic polyalkylenepolyamines) are prepared by amination of alcohols with reactant amines in the presence of $H_2$ and binary or ternary compounds of Group VIB metals as catalysts. Thus, 50 mL of a mixture of diethylenetriamine (I) and $H_2NCH_2CH_2OH$ (II) (mole ratio 2:1) was autoclaved over 6.3 g WB-WB2 catalyst at 315 and 365 psig $H_2$ for 5.0 h to show 36% conversion of II and the following selectivities (1- and II-free basis): $H_2NCH_2CH_2NH_2$ 19, triethylenetetramine 27, tetraethylenepentamine 36, piperazine 7, N-(2-aminoethyl)piperazine 9, and N-(2-aminoethyl)ethanolamine 1%.

U.S. Pat. No. 4,806,517 shows that linear polyethylenepolyamines are prepared by the condensation of ethylenediamine (I) with ethanolamine (II) over a catalyst which is prepared by impregnating Group IVB element oxide pellets with an aqueous solution of a P—O compd. at 20-150° C. so as to bond 0.5-6% of the P to the surface of the pellets in the form of hydroxy-containing phosphate groups, and then calcining at 200-900. A 100 mL solution of 85% $H_3PO_4$ was heated to 130° C. under an inert atmosphere, 105 cm3 of $TiO_2$ pellets were added, the mixture reacted for 2 h, and calcined at 600° C. for 16 h. The catalyst was contacted with a 2:1 molar ratio I-II mixt. of 325, producing approximately 65% II conversion with the formation (selectivity %) of piperazine 1.8, diethylenetriamine 59.0, N-(2-aminoethyl)ethanolamine 0.7, N-(2-aminoethyl)piperazine and N-(hydroxyethylpiperazine 2.1, triethylenetetramine 19.6, and tetraethylenepentamine 4.2%.

U.S. Pat. No. 4,584,405 Polyethylenepolyamines are prepared with high selectivity to linear products, from ethylenediamine (I) and ethanolamine (II) using activated C catalysts (optionally pretreated with strong mineral acids).

U.S. Pat. No. 4,552,961 Predominantly linearly extended polyalkylene polyamines are produced by treating alkylenediamines with alkylene glycols or alkanolamines using a P amide catalyst.

Other strategies use reductive amination methods in which alkanolamines are reacted with ammonia and/or alkyleneamines to produce cyclic triamines. Generally, only a small amount, e.g., less than 10 percent, of AEP is contained in the final product mixture. Examples of this practice using hydrogenation catalysts are described in U.S. Pat. Nos. 5,455,352; 5,248,827; and 4,602,091.

It remains desirable to develop strategies for making cyclic triamines with improved conversion and selectivity. It would also be desirable if the reaction conditions could be moderate in terms of temperature, and have improved catalyst stability.

SUMMARY OF THE INVENTION

The present invention provides strategies for making cyclic triamines. It has been discovered that reactant media including certain precursors and/or certain types of catalysts can be converted into cyclic triamines with improved conversion and selectivity. The strategies can be incorporated into reactions that involve transamination mechanisms and/or reductive amination mechanisms. In the case of transamination, for instance, using transamination to self-cyclize higher amines of the type including at least four amine moieties in the presence of a suitable catalyst leads to desired cyclic triamines with notable conversion and yield. In the case of reductive amination, co-reacting suitable precursors, such as alkanolamines with alkylene amines and/or ammonia, in the presence of a catalyst comprising Ni and Re also yields cyclic triamines with notable selectivity and conversion. Also, reductive amination mechanisms can also be used to self-cyclize polyfunctional reactants in the presence of a catalyst, optionally and preferably a catalyst comprising Ni and Re, causing the polyfunctional material to react with itself to effectively form the cyclic triamines. Preferred embodiments can produce reaction mixtures that are generally free of salt by-products.

In one aspect, the present invention relates to a method of making a cyclic triamine of the type comprising a cyclic moiety comprising first and second nitrogen backbone atoms and an N-amino moiety pendant from at least one of the nitrogen backbone atoms, comprising the steps of:
  a) providing a polyfunctional compound comprising one or more amine moieties, and, optionally, one or more nitrile moieties with the proviso that the sum of the amine and nitrile moieties is at least 4;
  b) causing ring closure of the polyfunctional compound in the presence of a catalyst under conditions effective to cause the polyfunctional compound to react with itself to form the cyclic triamine.

In another aspect, the present invention relates to a method of making a cyclic triamine of the type comprising a cyclic moiety comprising first and second nitrogen backbone atoms and an N-amino moiety pendant from at least one of the nitrogen backbone atoms, comprising the steps of:
  a) providing a tetraamine; and
  b) causing the ring closure of the tetraamine in the presence of a catalyst under conditions effective to cause the tetraamine to react with itself to form the cyclic triamine.

In another aspect, the present invention relates to a method of making a cyclic triamine of the type comprising a cyclic moiety comprising first and second nitrogen backbone atoms and an N-amino, moiety pendant from at least one of the nitrogen backbone atoms, comprising the step of reacting an alkanolamine with at least one of an alkyleneamine and/or ammonia in the presence of a catalyst comprising Ni and Re.

In another aspect, the present invention relates to a method of making a cyclic triamine of the type comprising a cyclic moiety comprising first and second nitrogen backbone atoms and an N-amino moiety pendant from at least one of the nitrogen backbone atoms, comprising the step of causing ring closure of a hydroxyl functional amine in the presence of a catalyst comprising Ni and Re under conditions effective to cause the hydroxyl functional amine to react with itself to form the cyclic triamine.

In another aspect, the present invention relates to a method of making a cyclic triamine of the type comprising a cyclic moiety comprising first and second nitrogen backbone atoms and an N-amino moiety pendant from at least one of the nitrogen backbone atoms, comprising the step of causing ring closure of a linear dihydroxyalkyleneamine in the presence of a catalyst under conditions effective to cause the linear dihydroxyalkyleneamine to react with itself to form the cyclic triamine.

In another aspect, the present invention relates to a method of making a cyclic triamine of the type comprising a cyclic moiety comprising first and second nitrogen backbone atoms and an N-amino moiety pendant from at least one of the nitrogen backbone atoms, comprising the step of causing ring closure of a branched dihydroxyalkyleneamine in the presence of a catalyst under conditions effective to cause the branched dihydroxyalkyleneamine to react with itself to form the cyclic triamine.

In another aspect, the present invention relates to a method of making a cyclic triamine of the type comprising a cyclic moiety comprising first and second nitrogen backbone atoms and an N-amino moiety pendant from at least one of the nitrogen backbone atoms, comprising the step of causing ring closure of a branched hydroxyalkyldialkylenetriamine in the presence of a catalyst under conditions effective to cause the branched hydroxyalkyldialkylenetriamine to react with itself to form the cyclic triamine.

In another aspect, the present invention relates to a method of making a cyclic triamine of the type comprising a cyclic moiety comprising first and second nitrogen backbone atoms and an N-amino moiety pendant from at least one of the nitrogen backbone atoms, comprising the step of causing ring closure of a linear hydroxyalkyldialkylenetriamine in the presence of a catalyst under conditions effective to cause the linear hydroxyalkyldialkylenetriamine to react with itself to form the cyclic triamine.

In another aspect, the present invention relates to a method of making a cyclic triamine of the type comprising a cyclic moiety comprising first and second nitrogen backbone atoms and an N-amino moiety pendant from at least one of the nitrogen backbone atoms, comprising the step of converting a hydroxyalkyl piperazine to the cyclic triamine in the presence of a catalyst comprising Ni and Re.

In another aspect, the present invention relates to a method of making a cyclic triamine of the type comprising a cyclic moiety comprising first and second nitrogen backbone atoms and an N-amino moiety pendant from at least one of the nitrogen backbone atoms, comprising the step of causing ring closure of a polyfunctional compound comprising at least one amine moiety and at least one nitrile moiety in the presence of a catalyst under conditions effective to cause the compound to react with itself to form the cyclic triamine.

In another aspect, the present invention relates to a method of making a cyclic triamine of the type comprising a cyclic moiety comprising first and second nitrogen backbone atoms and an N-amino moiety pendant from at least one of the nitrogen backbone atoms, comprising the steps of a) alkoxylating an amine or mixture of amines to provide a hydroxyalkyl functional amine comprising at least two amine groups and at least one hydroxyl group; and b) causing ring closure of the hydroxyalkyl functional amine in the presence of a catalyst under conditions effective to cause the compound to react with itself to form the cyclic triamine.

In another aspect, the present invention relates to a method of making a cyclic triamine of the type comprising a cyclic moiety comprising first and second nitrogen backbone atoms and an N-amino moiety pendant from at least one of the nitrogen backbone atoms, comprising the step of causing ring closure of a compound comprising at least two amine moieties and at least one hydroxyalkyl moiety in the presence of a catalyst under conditions effective to cause the compound to react with itself to form the cyclic triamine.

DETAILED DESCRIPTION OF PRESENTLY PREFERRED EMBODIMENTS

Reference will now be made in detail to representative embodiments of the invention. While the invention will be described in conjunction with the enumerated embodiments, it will be understood that they are not intended to limit the invention to those embodiments. On the contrary, the invention is intended to cover all alternatives, Modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods and materials described.

All publications and patents mentioned herein are incorporated herein by reference in their respective entireties for the purpose of describing and disclosing, for example, the constructs and methodologies that are described in the publications which might be used in connection with the presently described invention. The publications discussed above and throughout the text are provided solely for their disclosure prior to the filing date of the present application. Nothing herein is to be construed as an admission that the inventor is not entitled to antedate such disclosure by virtue of prior invention.

Unless defined otherwise, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

The present invention provides strategies for making cyclic triamines of the type comprising a cyclic moiety comprising first and second nitrogen backbone atoms and an N-amino moiety pendant from at least one of the nitrogen backbone atoms. The strategies can be used singly or in combination. The amine groups of the triamine can be primary, secondary, tertiary, or a combination of these. The cyclic triamine can be fully saturated or may include double bonds in the backbone of the cyclic moiety and/or in a moiety pendant from the cyclic moiety. Cyclic triamines may be substituted or non-substituted. As used herein "substituted" means that a moiety other than H is pendant to the backbone. "Non-substituted" means that, other than the N-amino moiety(ies), other substituents of the backbone are hydrogen.

Figure 1:
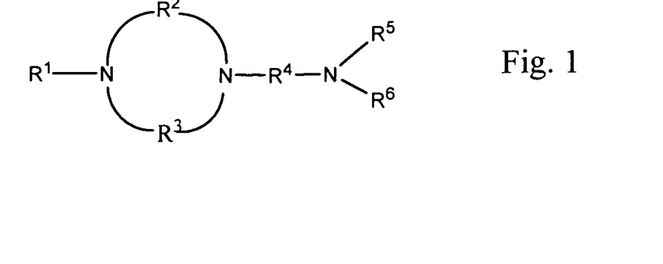
FIG. 1 shows a general formula for cyclic triamine.

In representative embodiments, cyclic triamines of the present invention are represented by the formula shown in FIG. 1, wherein each of $R^1$, $R^5$, and $R^6$ is independently a monovalent moiety or co-member of a ring structure but do not include N as a constituent of an amine moiety. Any of $R^1$, $R^5$, and $R^6$ may optionally include one or more heteroatoms other than N in the backbone or a moiety pendant from the backbone. Examples of moieties suitable as $R^1$, $R^5$, and $R^6$ include but are not limited to H; linear, branched, or cyclic hydrocarbyl such as alkyl, aryl, aralkyl, or the like; a monovalent moiety including one or more heteroatoms; polyether chains comprising one or more oxyalkylene repeating units such as —$R^{17}$O—, wherein $R^{17}$ is often alkylene of 2 to 5 carbon atoms; other oligomeric or polymer chains of at least 2 repeating units; —$R^{18}$N— wherein $R^{18}$ is alkylene of at least 2, preferably 2 to 5 carbon atoms. Preferably, each of $R^1$, $R^5$, and $R^6$ independently is H or straight, branched, or cyclic hydrocarbyl such as alkyl of 1 to 10 carbon atoms, preferably 1 to 3 carbon atoms. More preferably, each of $R^1$, $R^5$, and $R^6$ is H.

Each of $R^2$, $R^3$, and $R^4$ is independently any suitable divalent moiety that may be substituted or unsubstituted. Examples of suitable divalent moieties include linear, branched, or cyclic hydrocarbylene moieties such as alkylene, arylene, aralkylene, or the like; polyether chains comprising one or more oxyalkylene repeating units such as —$R^{17}$O—, wherein $R^{17}$ is often alkylene of 2 to 5 carbon atoms; other oligomeric or polymer chains of at least 2 repeating units; and/or —$R^{18}N$— wherein $R^{18}$ is alkylene of at least 2, preferably 2 to 5 carbon atoms. Preferably, each of $R^2$, $R^3$, and $R^4$ is independently an alkylene moiety of 2 to 20 carbon atoms, preferably 2 to 10 carbon atoms, often ethylene.

If any of $R^1$, $R^2$, $R^3$, $R^4$, $R^5$, or $R^6$ includes functional groups, these may be masked in accordance with conventional masking strategies to protect them in the course of the reaction described herein. After the reaction is completed, the functional groups can be unmasked if desired.

Figure 2:
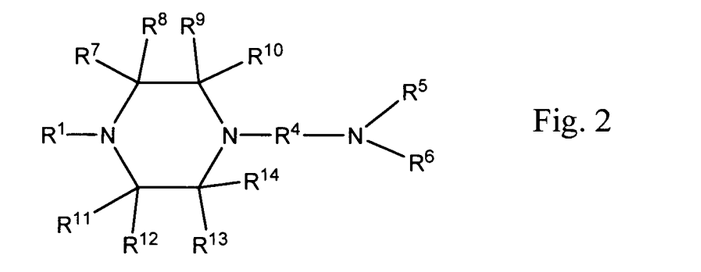
FIG. 2 shows a general formula for a cyclic triamine that incorporates a piperazine moiety.
Figure 3:
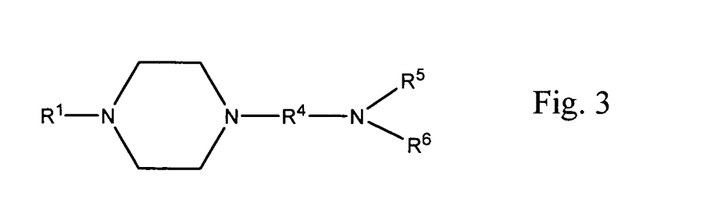
FIG. 3 shows a triamine that incorporates a piperazine moiety.

In preferred embodiments, the cyclic moiety incorporated into the cyclic triamine is a six-membered ring in which the two nitrogen backbone atoms are at positions 1 and 4 relative to each other in the ring and each nitrogen respectively constitutes a portion of an amine moiety. The other 4 atoms in the ring are carbon atoms. Further, an N-amino moiety is linked to at least one of these backbone nitrogens. Such a six-membered ring will be referred to herein as a piperazine moiety. In representative embodiments, a cyclic triamine incorporating a piperazine moiety has the formula shown in FIG. 2, wherein $R^1$, $R^4$, $R^5$, and $R^6$ are as defined above and each of $R^7$ through $R^{14}$ is independently a monovalent moiety or a co-member of a ring structure. Preferably, each of $R^7$ and $R^{14}$ is independently a monovalent moiety according to the definitions of $R^1$, $R^5$, and $R^6$. More preferably, each of $R^7$ through $R^{14}$ are hydrogen such that the cyclic amine has the formula shown in FIG. 3.

Figure 4:
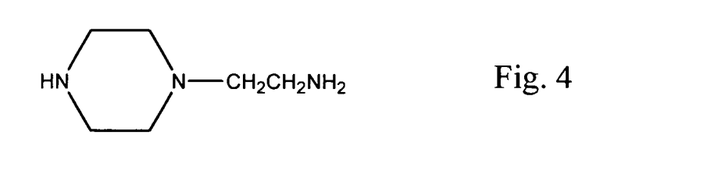
FIG. 4 shows an aminoethylpiperazine.

In a particularly preferred mode of practice, the cyclic triamine is aminoethylpiperazine of the formula shown in FIG. 4. This compound is commonly referred to as "AEP" and is unique for including a primary, secondary, and tertiary amine. AEP has many uses that include inhibition of corrosion, epoxy curing, surface activating, constituent of asphalt adhesive, mineral processing aid, and the like. AEP is also known by other names, including 2-piperazin-1-ylethaneamine; 2-(1-piperazinyl)ethylamine; N-AEP, N-(2-aminoethyl) piperazine; 2-piperazinoethylamine; 1-(2-aminoethyl)piperazine, 1-piperazine ethaneamine, and 1-aminoethylpiperazine.

In the practice of the present invention, cyclic triamines are formed by reacting one or more suitable precursors under conditions effective to achieve the desired product. In one preferred mode of practice, transamination techniques are used to convert amines having four or more amine moieties (hereinafter "higher amines") into the desired cyclic triamine. In another preferred mode of practice, reductive amination techniques are used to convert certain precursors into cyclic triamines. In another preferred mode, transamination and/or reductive amination techniques are used to form cyclic triamines from a wide range of precursors in the presence of a catalyst comprising Ni and Re. In still other modes of practice, combinations of two or more of these aspects can be practiced. For instance, it is advantageous to use a catalyst comprising Ni and Re in either transamination strategies of the invention, reductive amination strategies of the invention, or in inventive modes of practice in which a Ni and Re catalyst is incorporated into an otherwise conventional synthesis of cyclic triamines with improved results.

The methods of the present invention are selective for the desired product at high conversion of the precursor and selectivity for the desired product. For purposes of this invention, "conversion" refers to the total weight percentage of reactant lost as a result of reactions. The conversion can vary depending upon factors such as the reactants, catalyst, process conditions, and the like. In many embodiments, the conversion is at least about 2 weight percent, preferably at least about 10 weight percent, more preferably at least about 25 weight percent, most preferably at least about 35 weight percent.

For purposes of the invention, "selectivity" refers to the weight percentage of converted reactant(s) that form a desired cyclic triamine. Like conversion, selectivity will vary based upon factors including the reactants, catalyst, process conditions, and the like. In the practice of the present invention, selectivity for forming cyclic triamine in more preferred embodiments is at least about 10%, preferably at least about 25%, more preferably at least about 50%.

In preferred modes, the reaction occurs at moderate temperature with a moderate resultant, impurity load. Many leftover reactants, if any, and by-products, if any, have commercial value independent of the desired cyclic triamine product. After removing the desired product(s) from such mixtures, the remaining product mixture has many uses, including being recycled as a feed for the cyclization reaction, refined to recover some of the product(s) in more pure form, used as reactants in other reactions, used as is or with any desired modification as products such as epoxy curing agents, combinations of these, and the like.

The methods of the invention can be practiced in any suitable reactor. These include batch reactors, continuous fixed bed reactors, slurry bed reactors, fluidized bed reactors, catalytic distillation reactors, combinations of these, and the like.

According to one desirable methodology of the present invention for forming cyclic triamines, a higher amine is self-cyclized to from the cyclic triamine in the presence of a suitable catalyst via transamination techniques. Transamination generally refers to the transfer of one amine from one location to another. When two different reactants are subjected to a transamination reaction, an amine moiety is transferred from one molecule to the other. When a molecule is self-cyclized by reacting with itself, there is a transposition of an amino group within the molecule. Schematically, the reaction can be viewed as causing one of the amine moieties to be removed from the molecule, allowing the other amine to bond to the location vacated by the removed amine group.

Figure 5:
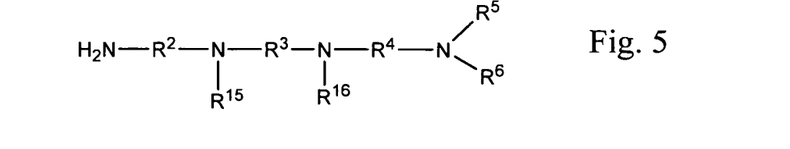
FIG. 5 shows a general formula for a linear higher amine.
Figure 6:
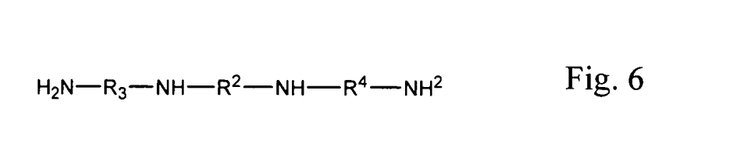
FIG. 6 shows a general formula for a linear tetraamine.

The polyfunctional compounds used in the transamination reaction of the present invention can include a combination of primary, secondary, and tertiary amine moieties, but it is desirable if at least two of the amine moieties are primary and/or secondary to facilitate self-cyclization. Reactants can include a combination of one or more of such higher amines. The higher amine in many embodiments is linear or branched. For instance, in exemplary embodiments, a representative class of linear higher amines may be represented by the general formula of the following class of tetraamines shown in FIG. 5, wherein each of $R^2$, $R^3$, $R^4$, $R^5$, and $R^6$ is independently as defined above, and each of $R^{15}$ and $R^{16}$ is independently a monovalent moiety according to the definitions for $R^1$, $R^5$, and $R^6$ above. In preferred embodiments, a linear tetraamine has the formula shown in FIG. 6, wherein each of $R^2$, $R^3$, and $R^4$ is each independently as defined above.

Figure 7:
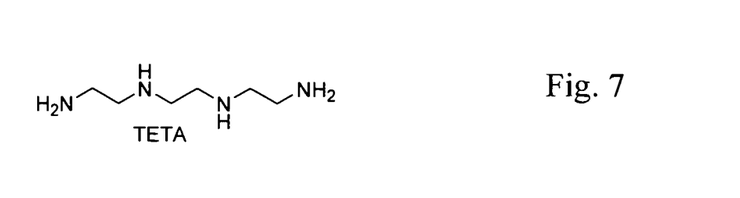
FIG. 7 shows the formula for linear triethyltetramine.

In a more preferred embodiment, a linear tetraamine has the formula shown in FIG. 7. This compound is known as linear triethylenetetraamine or L-TETA.

Figure 8:
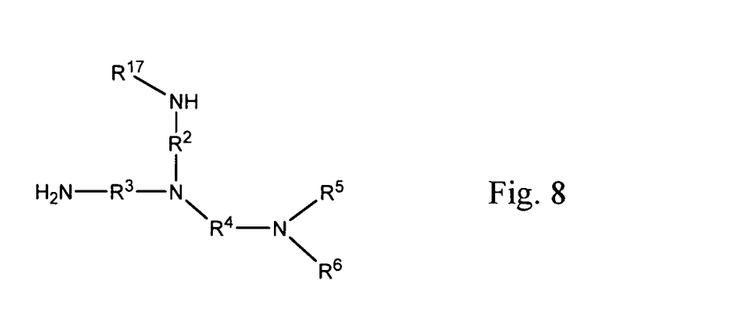
FIG. 8 shows a general formula for a branched higher amine.
Figure 9:
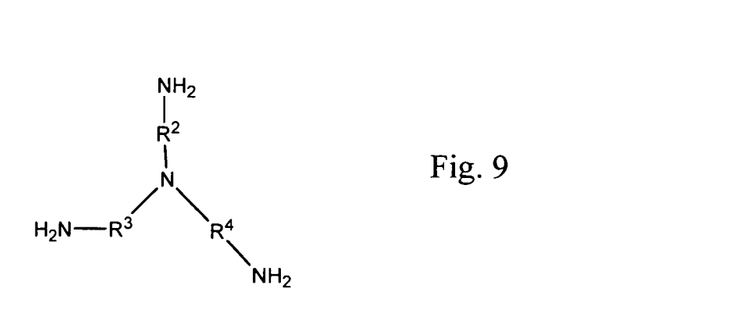
FIG. 9 shows a general formula for a branched higher amine.

In other exemplary embodiments, a representative class of branched higher amines may be represented by the general formula of the following class of tetraamines shown in FIG. 8, wherein each of $R^2$, $R^3$, $R^4$, $R^5$, and $R^6$ is independently as defined above, and $R^{17}$ is a monovalent moiety according to the definitions for $R^1$, $R^5$, and $R^6$ above. In preferred embodiments, a branched tetraamine has the formula shown in FIG. 9, wherein each of $R^2$, $R^3$, and $R^4$ is each independently as defined above.

Figure 10:
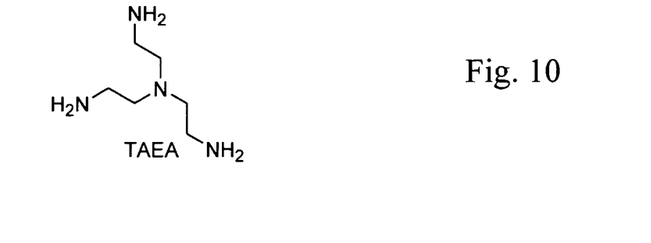
FIG. 10 shows a specific linear tetramine.

In a more preferred embodiment, a linear tetraamine has the formula shown in FIG. 10. This compound is known as trisaminoethylamine (TAEA). Other examples of higher amines include pentaamines such as tetraethylenepentaamine (TEPA), pentaethylenehexamine (PEHA), and other higher ethyleneamines generally referred to as heavy polyethyleneamines (HPA), combinations of these, and the like. Higher amines with cyclic moieties that can be cracked back to a cyclic triamine such as AEP also may be used.

Mixtures of higher amines can also be used. For instance, a suitable reaction medium might include a combination of L-TETA and TAEA wherein the weight ration of L-TETA to TAEA is in the range from 1:1000 to 1000:1, preferably 1:50 to 50:1, or even 1:5 to 5:1. While the above identified classes of higher amines and specific examples thereof are representative of those useful in the practice of the present invention, one or more other higher amines could be used as well, including those that are monomeric, oligomeric, or polymeric. As used herein, an oligomer refers to a compound incorporating 2 to 10 monomeric residues. A polymer refers to a compound incorporating more than 10 monomeric residues.

In an exemplary transamination reaction scheme, a reaction medium comprising one or more higher amine reactants is self cyclized. For instance, L-TETA and/or TAEA can be self-cyclized to produce AEP with ammonia as a by-product. Alternatively, a pentaamine such as TEPA can be self-cyclized to produce AEP with ethylenediamine (EDA) as a by-product.

The higher amine reactant(s) used in the self-cyclizing reaction can be supplied in substantially pure form or can be present with other ingredients, including other amines. For example, an output of an exemplary industrial process may be a mixture including one or more amines including at least one higher amine, desirably at least one of L-TETA and/or TAEA. Such mixture might even include a desired cyclic triamine such as some AEP. Such a mixture can be used as a reactant mixture in the practice of the invention. The product mixture will be enriched with cyclic triamine content relative to the starting reaction medium.

As just one example, an illustrative output of an industrial process might include ethylenediamine (EDA), piperazine (PIP), diethylenetriamine (DETA), AEP, L-TETA, N-(piperazinoethyl)ethylenediamine (PEEDA), Tetraethylenepentamine (L-TEPA), and others. This mixture can be processed in the practice of the present invention to increase the AEP content. Optionally, one or more of the amines of such a starting mixture, including the AEP, can be removed prior to being subjected to the transamination reaction. Examples of enriching the AEP content of such a mixture and other mixtures as well are provided below.

Figure 11:
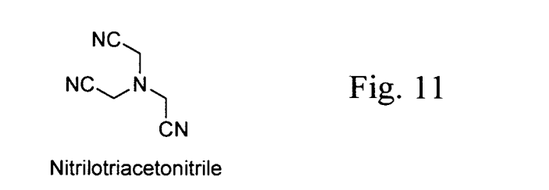
FIG. 11 shows a formula for nitrilotriacetonitrile.

Nitrile functional amine precursors can also be used in the transamination methodologies. In the course of the transamination, the nitrile groups can react with amines to give cyclic compounds, or may be converted to imines which can react with amines to give cyclic compounds or be reduced to the amine which can then proceed to cyclize via transamination. A nitrile functional amine precursor is a compound comprising at least one amine moiety and at least one nitrile moiety with the proviso that the sum of the amine and nitrile groups is at least 4. An illustrative nitrile functional amine is nitrilotriacetonitrile. This compound has the structure shown in FIG. 11.

In addition to transamination strategies, alternative methodologies of the invention involve using reductive amination techniques, optionally in combination with transamination mechanisms, to convert suitable precursors into a cyclic triamine. Optionally and preferably, the reductive amination strategies may occur in the presence of a catalyst comprising Ni and Re (embodiments of this catalyst are described further below). Advantageously, the use of a catalyst comprising Ni and Re to carry out these reactions provides cyclic triamines such as AEP at high levels in the final product mix with very good selectivity. Cyclic triamines can be produced under much milder temperatures as compared to comparable processes that use only alternative catalysts. Preferred embodiments of the invention can be practiced without using halogenated reactants, avoiding undue production of salts.

According to one approach that incorporates reductive amination techniques, two or more reactants are co-reacted to form cyclic triamines. For instance, ammonia and/or one or more alkyleneamines is/are reacted with one or more alkanolamines optionally in the presence of a reducing agent and a catalyst such as one comprising Ni and Re. In addition to catalysts comprising Ni and Re, other catalysts in accordance with conventional strategies can also be used, if desired. Catalysts used in conventional reductive amination strategies using ammonia, ethyleneamines, and ethanolamines to form cyclic triamines are described in U.S. Pat. Nos. 5,248,827; 5,248,827; and 4,602,091, for example.

An alkyleneamine is a compound comprising at least one linear, branched, or cyclic alkylene moiety and at least two amine moieties. The amine moieties preferably are primary or secondary to facilitate the desired reaction. In addition to the amine moieties, the backbone may also incorporate one or more additional amines. Desirably, the alkylene moiety is divalent and includes from 2 to 20, preferably 2 to 10, more preferably 2 to 5 carbon atoms. Of these, ethylene, $CH_2CH_2$—, is preferred.

Representative examples of alkyleneamines include ethylenediamine, diethylenetriamine, triethylenetetramine, tetraethylenepentaamine, pentaethylenehexamine, piperazine, and HPA, combinations of these, and the like. Ammonia, if used, may be anhydrous or may be supplied in aqueous form.

The alkanolamine is a compound that includes at least one linear, branched, or cyclic alkylene chain, at least one hydroxyl group, and at least one amine moiety. In preferred embodiments, the alkylene chain has from 2 to 20, preferably 1 to 10, more preferably 2 to 5 carbon atoms. Of these, ethylene, —$CH_2CH_2$—, is preferred. Examples include monoethanolamine, diethanolamine, triethanolamine, hydroxyethylpiperazine, N-(2-aminoethyl)ethanolamine, monoisopropanolamine, diisopropanolamine, triisopropanolamine, combinations of these, and the like.

With respect to the ratio of starting materials to be used in the reductive amination processes, the molar ratio of alkyleneamine when present to the alkanolamine is preferably from 0.1 to 20, more preferably 0.5 to 10; and the molar ratio of ammonia when present is preferably from 1 to 50, more preferably from 3 to 40, most preferably from 5 to 30. When using ammonia as a reactant, a stoichiometric excess of ammonia is most desired. In the case of reacting an ethanolamine with an ethylene amine, using about the stoichiometric ratio is most desired.

According to another approach, a suitable precursor is reacted with itself, wherein the precursor comprises at least one amine group, at least one OH group, and optionally at least one other pendant nucleophilic moiety such as nitrile, amine, or hydroxyl group, or the like, with the proviso that the sum of the amine, OH, and optional additional nucleophilic moieties (if any) is at least 3, preferably 3 to 12, more preferably 3 to 5. Such precursors shall be referred to herein as polyfunctional precursors. In preferred embodiments, this approach is practiced using catalysts comprising Ni and Re optionally in combination with one or more other catalysts if desired.

Figure 12:
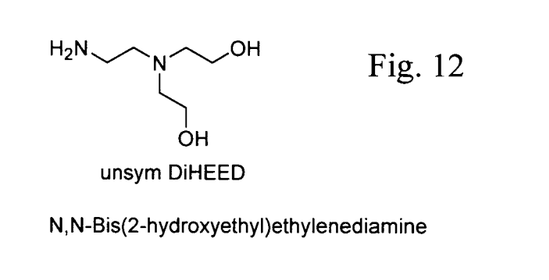
FIG. 12 shows the formula for N,N-dihydroxyethylethylenediamine.
Figure 13:
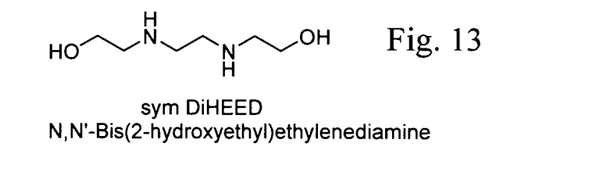
FIG. 13 shows the formula for N,N'-dihydroxyethylethylenediamine.
Figure 14:
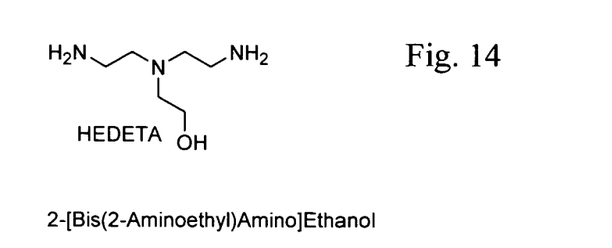
FIG. 14 shows the formula for branched hydroxyethyldiethylenetriamine.
Figure 15:
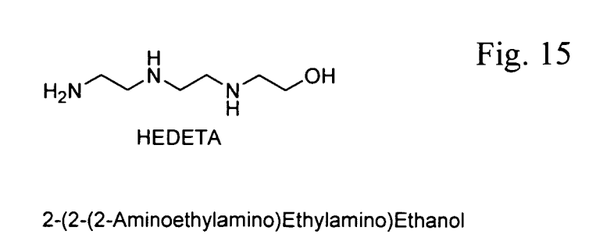
FIG. 15 shows the formula for linear hydroxyethyldiethylenetriamine.
Figure 16:
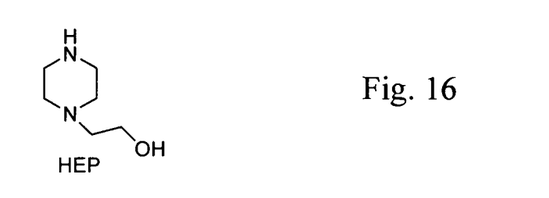
FIG. 16 shows the formula for hydroxyethyl piperazine.
Figure 17:
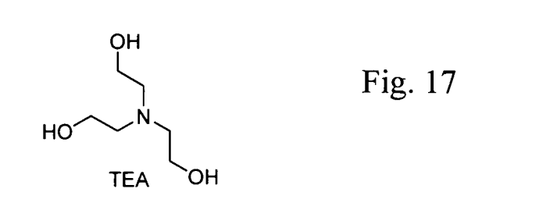
FIG. 17 shows the formula for triethanolamine.

A wide variety of multifunctional precursors may be used in the practice of the present invention. Representative examples include N,N-dihydroxyethylethylenediamine (unsym DiHEED) having the formula shown in FIG. 12, N,N'-dihydroxyethylethyleneamine (sym DiHEED) having the formula shown in FIG. 13, branched hydroxyethyldiethylenetriamine (b-HEDETA) having the formula shown in FIG. 14, linear hydroxyethyldiethylenetriamine (l-HEDETA) having the formula shown in FIG. 15, hydroxyethyl piperazine (HEP) having the formula shown in FIG. 16, and triethanolamine (TEA) having the formula shown in FIG. 17.

In the above polyfunctional precursors, all of the divalent linking groups between the functional amine and OH groups are the divalent moiety ethylene. In alternative embodiments, any other suitable linear or branched divalent linking groups, or combinations of groups, could be used. Examples include any of the divalent moieties defined above with respect to $R^2$, $R^3$, and $R^4$.

Compounds including both amine and another nucleophilic moiety such as hydroxyl can be converted to cyclic triamine via two or more pathways. For instance, in the case of b-HEDEETA, the two primary amine moieties could cyclize via a transamination mechanism. The OH of the pendant N-hydroxyethylene group could then be converted to amine by a reductive amination mechanism. Alternatively, one of the primary amines could react with the pendant hydroxyl group to cyclize via a reductive amination mechanism. Optionally, ammonia can be present when practicing these reactions to promote the occurrence of both reaction mechanisms.

In many embodiments, the amine mixture used as a starting reaction material for either transamination or reductive amination will be in liquid form such that no additional solvent is needed. Indeed, in many instances it may be preferred to carry out the desired reaction in the absence of solvent. However, one or more solvents may be used if desired. A variety of solvents or combinations of solvents may be used. Desirably, the solvent is not unduly reactive with the higher amine reactant(s) or cyclic triamine product(s) and does not unduly decompose under the reaction conditions. Some examples of solvents that could be used include saturated hydrocarbons such as pentane, hexane, octane, nonane, decane, or the like; aromatic hydrocarbons such as toluene, benzene, xylene, ether, combinations of these, and the like. Alcohols are desirably avoided, as many of these are capable of reacting with the amine reactants and/or products. If present, the amount of solvent used may vary over a wide range. In a typical instance, the solvent may constitute from about 5 to about 98 weight percent, desirably 10 to 80 weight percent, of the mixture. Optionally when solvent is used, the reaction medium can be diluted to favor intramolecular reactions and, hence, cyclization, relative to intermolecular interactions.

A variety of catalysts can be used in the practice of the present invention for either transamination or reductive amination. Catalysts can be acidic, alkaline, neutral, or a combination of different catalysts can be used. Representative classes of catalyst metals, alloys, intermetallic compositions, or molecules (such as oxides, nitrides, phosphates, silicates, and the like, or mixtures of one or more transition metals, including the lanthanoid and/or actinoid series. A wide variety of catalysts applicable to amine chemistry are described in U.S. Pat. Nos. 6,534,441; 5,256,786; 5,073,635; 4,983,735; 5,030,740; 4,927,931; 5,222,599; 4,906,782; 4,922,024; 4,806,517; 4,584,405; 4,552,961; 5,455,352; 5,248,827; 4,602,091. See also Russian patents 2226188 and 2186761. The catalyst(s) can be present as metals, alloys, mixtures, intermetallic compositions, as compounds such as oxides, hydroxides, salts, alkoxides, silicates, phosphates, as complexes, or the like.

In a preferred embodiment, the catalyst incorporates one or more hydrogenation and/or dehydrogenation catalysts. Hydrogenation generally refers to a chemical reaction involving the addition of hydrogen, and the process is often used to reduce or saturate organic materials. The reverse reaction in which hydrogen is removed from an organic molecule is referred to as dehydrogenation. The use of hydrogenation and/or dehydrogenation catalysts has been found to be useful for transamination and reductive amination in the practice of the present invention.

A wide variety of hydrogenation/dehydrogenation catalysts are known. Platinum group metals, particularly platinum, palladium, rhodium, and ruthenium form highly active hydrogenation/dehydrogenation catalysts. These are known to operate at lower temperatures and lower pressures of $H_2$. Non-precious metal catalysts, especially those based on nickel (such as Raney nickel and Urushibara nickel) have also been developed as economical alternatives. Other hydrogenation/dehydrogenaton catalysts might incorporate iron, copper, chromium, molybdenum, cobalt, osmium, iridium, and/or the like.

In particularly preferred embodiments, the catalyst material incorporates hydrogenation/dehydrogenation catalytic ingredients comprising nickel and rhenium. The weight ratio of nickel to rhenium may vary over a wide range. For instance, the weight ratio of nickel to rhenium may be in the range from about 1:1000 to 1000:1, preferably 1:100 to 100:1, more preferably 1:50 to 50:1. Even more desirably, the weight ratio of nickel to rhenium is within these ranges with the proviso that the weight ratio is also greater than 1:1. In illustrative embodiments, using a weight ratio from about 3:1 to 10:1 would be suitable. In preferred embodiments in which a heterogeneous catalyst incorporates nickel and rhenium, a useful support are alumina-silicate particles. Such catalysts and methods of making such heterogeneous catalysts on such supports are further described in U.S. Pat. No. 6,534,441. Such catalysts are also further described in Assignee's co-pending U.S. patent application Ser. No. 12/587,335 titled "LOW METAL LOADED, ALUMINA SUPPORTED, CATALYST COMPOSITIONS AND AMINATION PROCESS" by Steven W. King et al. and filed co-currently with the present application. Additional suitable catalysts are also described in Assignee's co-pending U.S. patent application Ser. No. 12/587,351 titled "LOW METAL CATALYST COMPOSITIONS INCLUDING ACIDIC MIXED METAL OXIDE AS SUPPORT" by Steven W. King et al. also filed co-currently herewith.

Additional catalysts suitable in the practice of the invention are also described in Assignee's co-pending U.S. Patent Application titled "Cobalt Catalysts for Amine Conversion", bearing Ser. No. 12/587,355 in the names of Stephen W. King et al, filed co-currently with the present application.

Catalysts can be heterogeneous, homogeneous, or a combination of these may be used. Homogeneous catalysts dissolve in the reaction medium. Illustrative homogeneous catalysts include the rhodium-based compound known as Wilkinson's catalyst and the iridium-based Crabtree's catalyst. Heterogeneous catalysts are solids that are caused to contact the reaction medium, which may be in liquid, gas or other fluid form.

Heterogeneous catalysts are preferred. Often, heterogeneous catalysts comprise one or more catalytic materials supported upon a suitable substrate. The substrate may be used in various shapes or combinations such as, for example, powder, particle, pellet, granule, extrudate, fiber, shell, honeycomb, plate, or the like. The particles can be regular in shape, irregular, dendritic, dendrite-free, or the like. Preferred supports are particulate in nature or powders.

Particulate support may have a so-called guest/host structure which may be prepared by adsorbing or adhering fine (less than 100 micrometers, preferably less than 50 micrometers and most preferably less than 10 micrometer in size) nanoporous particles on coarser (greater than 30 mesh) particles. The smaller particles are referred to as guests, while the large particles supporting them are referred to as hosts. This small-particle-supported-on-a-larger-particle composite structure provides very high total exterior surface area while retaining the desirable gas passing characteristics, i.e., low pressure drop, of a coarser particle. In addition, by using smaller particles in constructing these composite particles, inexpensive, coarser particles can be used. Thus, very inexpensive, highly active catalyst particles can be prepared since the bulk of the volume of a catalyst bed may be taken up by the inexpensive, underlying, coarser particles.

The catalyst material can be incorporated into or onto the guest and/or host particles. Often, the catalyst material is incorporated mainly onto the guest material before or after the guest/host composite is formed. Guest/host structures and methods of making these are further described in U.S. Publication No. 2005-0095189 A1.

Preferably, the catalyst and/or the supported catalyst composition is calcined prior to use. Generally, calcining can occur in air or an inert atmosphere such as one based upon nitrogen, argon, carbon dioxide, combinations of these, and the like. Calcining can occur at a variety of elevated temperatures, such as a temperature up to about 1000° C., preferably about 200° C. to about 800° C.

A wide variety of materials may serve as suitable supports in the practice of the present invention. Representative examples include carbonaceous materials, silicaceous materials (such as silica), metal compounds such as metal oxides, combinations of these, and the like. Representative metal oxides include oxides of one or more of magnesium, aluminum, titanium, vanadium, chromium, manganese, iron, cobalt, nickel, copper, zinc, gallium, germanium, strontium, yttrium, zirconium, niobium, molybdenum, technetium, ruthenium, rhodium, palladium, silver, cadmium, indium, iron, tin, antimony, barium, lanthanum, hafnium, thallium, tungsten, rhenium, osmium, iridium, and platinum.

Examples of carbonaceous substances include activated carbon and graphite. Suitable activated carbon particles may be derived from a wide variety of source(s) including coal, coconut, peat, any activated carbon(s) from any source(s), combinations of at least two of these, and/or the like.

Catalyst material may be incorporated into heterogeneous catalyst systems in a variety of ways. In some instances, a catalyst precursor is first provided on the support, and then the precursor can be converted into the catalyst itself afterward. Exemplary procedures are well known in the industry and include solution impregnation, precipitation, vapor deposition such as by PVD or CVD techniques, and the like.

The amount of catalyst used in forming a cyclic triamine using either transamination or reductive amination strategies is any amount which is effective in producing the desire cyclic triamine. For batch conditions, the quantity of catalyst may be in the range from about 0.1 to about 20 weight percent, preferably 1 to 15 weight percent, of catalyst per 100 parts by weight of reactant(s) to be self-cyclized to form the desired triamine. In a continuous process, a typical strategy might involve causing a flow of reactants to contact a bed of heterogeneous catalyst particles. In such a case, the space velocity (usually expressed in units of gmol/(kg catalyst/hr) can be adjusted to balance factors such as production and selectivity.

When calculating the weight percent of catalyst for batch or continuous processes, only the actual amount of active catalytic substance is used to determine the weight percent of catalyst. For instance, in an exemplary embodiment, 100 parts by weight of heterogeneous catalyst particles might be used to treat a mixture containing 91 parts by weight of L-TETA and 9 parts by weight of TAEA. Other amines may or may not be present in the mix: The total amount of reactants is 100 parts by weight. The heterogenous catalyst particles might include 5 part by weight of Ni and 1 part by weight of Re as metals for a total of 6 parts by weight of catalyst. In this case, the batch reactor would include 6 parts by weight of the catalyst per 100 parts by weight of the reactants. For purposes of the present invention, if the catalyst is present as a molecule such as an oxide or the like, only the weight of the active metal catalyst constituent is used to determine the weight percent.

The reactant mixture for either transamination or reductive amination optionally may include hydrogen. For reductive amination in particular, the presence of hydrogen can help keep the catalyst active. When hydrogen is used, the level of hydrogen can be adjusted to favor ring closure. Generally, a lower hydrogen concentration favors ring closure. From 0 to about 50 mole percent, desirably 0.1 to 25 mole percent of hydrogen per mole of reactants would be suitable. The reactant mixture for either transamination or reductive amination optionally may include ammonia. Ammonia can help suppress the production of undesired by-products, particularly in transamination. Ammonia can be a reactant in either transamination or reductive amination. From 0 to about 100 mole percent, desirably 1 to 25 mole percent of ammonia per mole of reactants would be suitable. In addition to the desired reactant amine(s), the reaction mixture optionally may include one or more additional amines. If these are not reactive in a way to produce the desired cyclic triamine, such amines are not considered amines hereunder. Such other amines are present as a practical matter, for instance, when the feed used in the processes of the present invention is obtained as the output of an industrial process. The present invention can be used to process this output to increase the cyclic triamine content. The output can be used as is as a feed herein or can be processed first, as desired, such as to remove one or more constituents prior to enrichment.

For example, an output of an industrial process may be a mixture including one or more amines including at least one tetramine, desirably at least one of L-TETA and TAEA if transamination techniques are used. Such mixture might even include a desired cyclic triamine such as some AEP. Such a mixture can be used as a reactant mixture in the practice of the invention to enrich the cyclic triamine content. As just one example, an illustrative output of an industrial process might include ethylenediamine (EDA), piperazine (PIP), diethylenetriamine (DETA), AEP, L-TETA, N-(piperazinoethyl)ethylenediamine (PEEDA), Tetraethylenepentamine (L-TEPA), and others. This mixture can be processed in the practice of the present invention to increase the AEP content. Optionally, one or more of the amines of such a starting mixture, including the AEP, can be removed prior to being subjected to the transamination reaction. Examples of enriching the AEP content of such a mixture and other mixtures in the context of both transamination and reductive amination are provided below. Some of the amine constituents of such a mixture can react to make higher amines. These higher amines can ring close to yield a cyclic triamine such as AEP and a by-product such as ammonia or an amine.

The reaction mixture for either transamination or reductive amination can be contacted with catalyst at any suitable temperature(s) that promote the ring closure reaction to produce the desired cyclic triamine. Typically, the temperature is maintained below about 350° C., preferably below 300° C. Preferred temperatures are in the range from about 130° C. to about 170° C. for transamination and about 160° C. to about 200° C. for reductive amination: Below the preferred temperature ranges, the conversion to cyclic triamine may be too slow to be practical for commercial scale production. Above the preferred temperature ranges, selectivity may be reduced to an undue degree, increasing the yield of by-products. In some instances, such by-products may have commercial value and be desirable as a consequence. In other instances, by-products constitute impurities as a practical matter.

Similarly, the reaction mixture for either transamination or reductive amination can be contacted with catalyst at any suitable pressure(s) that promotes the cyclization reaction to produce the desired cyclic triamine. Preferably, the pressure is sufficient to maintain the reactor contents in a liquid state as the reaction proceeds. In many instances, the pressure will vary as the reaction proceeds. For instance, ammonia is a by-product of a typical transamination process. The production of ammonia causes the pressure generally to increase as the reaction proceeds. Ammonia and/or other pressure-increasing products can be removed from the reactor in order to keep the pressure below a desired threshold.

Typically, the pressure is in the range from about 0 psi to about 5000 psi, preferably 10 psi to 3000 psi, more preferably 100 psi to 1000 psi. For reductive amination, pressures in the range of 1200 psi to 2400 psi are preferred. For transamination, pressures in the range of 400 psi to 800 psi are preferred.

In one mode of practice, precursors can be converted into suitable starting materials, which are then converted to cyclic triamines via transamination and/or reductive amination reactions. According to one approach, an amine or a mixture of amines can be alkoxylated to form starting materials. For example, a stream containing EDA and DETA can be ethoxylated to give a mixture including symmetrical and/or unsymmetrical DiHEED and linear and/or branched hydroxyethyl DETA. These product intermediates can be converted to cyclic triamines as described herein using reductive amination and/or transamination techniques.

The following Assignee co-pending applications filed co-currently herewith describe technology relating to catalysts, reductive amination, and/or transamination. Each is incorporated herein by reference in its respective entirety for all purposes.

1. Ser. No. 12/587,355 titled "Low Metal Loaded, Alumina Supported, Catalyst Compositions and Amination Process" by Stephen W. King et al.
2. Ser. No. 12/587,351 titled "Low Metal Catalyst Compositions Including Acidic Mixed Metal Oxide as Support" by Steven W. King et al.
3. Ser. No. 12/587,372 titled "A Process to Selectively Manufacture Diethylenetriamine (Deta) or Other Desirable Ethyleneamines Via Continuous Transamination of Ethylenediamine (Eda), and Other Ethyleneamines Over a Heterogeneous Catalyst System" by Ronald Gary Cook et al.
4. Ser. No. 12/587,358 titled "Methods for Making Ethanolamine(s) and Ethyleneamine(s) From Ethylene Oxide and Ammonia, and Related Methods" by David Do et al.
5. Ser. No. 12/587,350 titled "Method of Manufacturing Ethyleneamines" by David M. Petraitis et al.

The present invention will now be further described with reference to the following illustrative examples.

Example 1

A catalyst was prepared by an incipient wetness technique using two impregnations. A solution of 107.6 grams of nickel nitrate hexahydrate (Aldrich no. 244074; crystal, 98%) and 8.26 grams of ammonium perrhenate (Molymet) in 318 ml deionized water was prepared. The solution was heated to 70° C. 193 ml of the solution was added to 297.0 grams of a pre-dried alumina/silica carrier ($Al_2O_3/SiO_2$, 80:20, 1/16" extrudate, SA=153 $m^2/g$), followed by calcination in air at 340° C. for 2 hours. A second impregnation using the remaining solution (188 ml) was followed by calcination at 340° C. for 3 hours. The catalyst was reduced at 340° C. in flowing hydrogen at a flow rate of ~1600 cc/min for three hours. Following the reduction, the catalyst was allowed to cool to room temperature and passivated using 1% oxygen in nitrogen to allow handling in air. The final yield was 325.5 grams of catalyst with a nominal composition of 6.8 wt. % nickel and 1.8 wt. % rhenium on alumina-silica.

The catalyst was used to convert L-TETA to AEP. The L-TETA was supplied in a reaction mixture including other amines per Table A. Seven runs were performed at different, respective temperatures ranging from 120° C. to 155° C. Each reaction took place over 295 grams of catalyst described above loaded into 86.25" of 0.688" ID stainless steel tubing. A temperature traverse from 120-155° C. was conducted with an amine feed rate of 500~1000 gmole/hr/kg-cat, and H2 flow at 9-10 slph (about 10× hydrogen necessary to saturate the feed). All testing was done at 800 psig. The liquid product was collected in a receiver, the ammonia was weathered off and the product mix analyzed by capillary gas chromatography.

TABLE A

|  | | Temp, ° C.: | | | | | | |
|---|---|---|---|---|---|---|---|---|
|  | | 120 | 135 | 144 | 154 | 155 | 150 | 145 |
|  | | | | | Run no. | | | |
| GC results, wt % | Feed | 1 | 2 | 3 | 4 | 5 | 6 | 7 |
| EDA | 0 | 0.2107 | 0.5494 | 0.9096 | 1.8311 | 1.7375 | 1.3635 | 0.8512 |
| Piperazine | 0.008 | 0.0412 | 0.2568 | 1.8161 | 5.5513 | 5.2866 | 3.3932 | 1.6659 |
| DETA | 4.1921 | 4.2671 | 4.2836 | 4.3508 | 3.6426 | 3.6183 | 4.2096 | 4.3645 |
| AEP | 11.0877 | 12.2184 | 13.5185 | 20.3779 | 34.3297 | 33.3863 | 26.3092 | 19.5101 |
| L-TETA | 71.8928 | 71.1804 | 69.1141 | 54.6221 | 26.891 | 27.545 | 42.3373 | 55.7212 |
| PEEDA | 1.0527 | 1.1101 | 1.3597 | 2.8451 | 7.7807 | 7.4208 | 0.043 | 0.0159 |
| L-TEPA | 7.9535 | 7.9258 | 8.098 | 8.296 | 6.8927 | 6.816 | 8.0667 | 8.1914 |
| Other Amines | 3.81 | 3.05 | 2.82 | 6.79 | 13.09 | 14.19 | 14.28 | 9.68 |

As the table shows conversion of L-TETA produces a significant amount of AEP in the resultant product mix. As conversion levels increase AEP and other materials convert to higher ethyleneamines.

Example 2

Various materials were also evaluated in a batch mode as reported in this and the ensuing examples unless otherwise expressly noted. The reactions were conducted in a 2 L high-pressure 316SS autoclave (Autoclave Engineers) equipped with a magnetic stirrer, a dip tube for sampling, and a catalyst basket. Catalyst of Example 1 was charged to the catalyst basket and activated overnight with flowing hydrogen at 180° C. The autoclave was cooled to room temperature, and the liquid reactants charged by pressure, followed by ammonia (optional), taking care not to admit air. The autoclave was brought to operating pressure with hydrogen, and heated to operating temperature with stirring. Pressure was adjusted during the run, if necessary, by bleeding off or adding hydrogen to the autoclave. Samples were taken hourly via the dip tube and analyzed by GC. Prior to analysis, ammonia (if present) was weathered off.

Table 1 gives the results from reacting 900 grams of EDA with 100 grams of a Ni/Re catalyst at 160 C and an initial hydrogen pressure of 100 psig. The pressure of the reactor during the run was 170 to 730 psig. As can be seen from the table, AEP increases with EDA conversion, but still represents only a small portion (<5 percent) of the product mix even at high EDA conversion. Still, the amount of AEP in the product mix was enriched by almost 300% relative to the reactant mixture. On an industrial scale, depending on the size of the commercial unit, this can result in a significant amount of extra pounds of AEP on an annual basis.

TABLE 1

Catalyst: Ni/Re (6.8/1.8 wt. %) on alumina/silica 80:20

| | Run no. | | | | |
|---|---|---|---|---|---|
| | 1 | 2 | 3 | 4 | 5 |
| | | | Time, hrs | | |
| | 2 | 3 | 4 | 5 | 6 |
| | | | Temp, ° C. | | |
| | 160 | 159 | 162 | 162 | 162 |
| GC results | | | | | |
| EDA | 73.92 | 65.14 | 57.61 | 50.68 | 45.20 |
| PIP | 8.03 | 11.14 | 14.07 | 17.29 | 19.58 |
| DETA | 13.39 | 16.79 | 19.31 | 20.68 | 21.33 |
| AEP | 1.16 | 2.03 | 2.88 | 3.78 | 4.83 |
| I-TETA | 1.52 | 2.27 | 3.03 | 3.63 | 4.14 |
| PEEDA | 0.20 | 0.35 | 0.51 | 0.74 | 1.06 |
| I-TEPA | 0.26 | 0.47 | 0.63 | 0.85 | 1.04 |
| OTHERS | 1.53 | 1.81 | 1.98 | 2.35 | 2.82 |
| ~EDA Conversion, % | 29.41 | 38.79 | 46.63 | 53.65 | 59.05 |
| Wt % in Product (EDA free) | | | | | |
| PIP | 30.79 | 31.96 | 33.19 | 35.06 | 35.74 |
| DETA | 51.35 | 48.18 | 45.55 | 41.93 | 38.93 |
| AEP | 4.44 | 5.82 | 6.78 | 7.67 | 8.82 |
| I-TETA | 5.84 | 6.52 | 7.14 | 7.36 | 7.55 |
| Other Amines | 7.59 | 7.53 | 7.34 | 7.98 | 8.96 |
| | 100.00 | 100.00 | 100.00 | 100.00 | 100.00 |

Example 3

Table 2 gives the results from reacting 844 grams of EDA with 100 grams of a commercial nickel on silica/alumina catalyst at 145-158° C. and an initial hydrogen pressure of 270 psig but otherwise using the procedures of Example 2. The pressure of the reactor during the run was 800 to 1135 psig. As can be seen from the table, AEP increases with EDA conversion. These conditions produced less AEP at a given EDA conversion than those in Table 1 above.

TABLE 2

Catalyst: Sud-Chemie C46-7-03, 50% Ni on silica/alumina

| | Run no. | | | | | |
|---|---|---|---|---|---|---|
| | 1 | 2 | 3 | 4 | 5 | 6 |
| | | | Time, hrs | | | |
| | 1 | 2 | 3 | 4 | 5 | 6 |
| | | | Temp, ° C. | | | |
| | 156 | 152 | 154 | 145 | 147 | 158 |
| GC results | | | | | | |
| EDA | 91.91 | 80.96 | 77.02 | 70.97 | 63.51 | 54.66 |
| PIP | 0.29 | 1.27 | 1.93 | 3.20 | 5.46 | 9.09 |
| DETA | 7.24 | 15.34 | 17.67 | 20.67 | 23.47 | 25.10 |
| AEP | 0.01 | 0.07 | 0.11 | 0.21 | 0.49 | 1.07 |
| I-TETA | 0.40 | 1.72 | 2.34 | 3.45 | 4.82 | 6.37 |
| PEEDA | 0.01 | 0.02 | 0.03 | 0.07 | 0.17 | 0.44 |
| I-TEPA | 0.09 | 0.53 | 0.76 | 1.20 | 1.62 | 2.30 |
| OTHER AMINES | 0.06 | 0.10 | 0.13 | 0.22 | 0.46 | 0.98 |
| ~EDA Conversion, % | 9.46 | 21.84 | 26.20 | 32.80 | 40.75 | 49.87 |
| Wt % in Product (EDA free) | | | | | | |
| PIP | 3.53 | 6.65 | 8.38 | 11.01 | 14.97 | 20.05 |
| DETA | 89.46 | 80.57 | 76.91 | 71.22 | 64.33 | 55.37 |
| AEP | 0.10 | 0.35 | 0.48 | 0.73 | 1.34 | 2.36 |
| I-TETA | 4.97 | 9.03 | 10.20 | 11.88 | 13.20 | 14.04 |
| Other Amines | 1.93 | 3.38 | 4.03 | 5.16 | 6.17 | 8.18 |
| | 100.00 | 100.00 | 100.00 | 100.00 | 100.00 | 100.00 |

Example 4

Table 3 gives the results from reacting 740 grams of EDA with 100 grams of a commercial nickel on silica catalyst at 160-185° C. and an initial hydrogen pressure of 236 psig but otherwise using the procedures of Example 2. The pressure of the reactor during the run was 960 to 2140 psig. As can be seen from the table, AEP increases with EDA conversion. These conditions produced more AEP at a given EDA conversion than those in Table 2, but less than the process conditions for Table 1.

TABLE 3

Catalyst: Engelhard Ni-5256E 57% Ni on silica ⅛" extrudate

| | Run no. | | | | | | |
|---|---|---|---|---|---|---|---|
| | 1 | 2 | 3 | 4 | 5 | 6 | 7 |
| | | | | Time, hrs | | | |
| | 1 | 2 | 3 | 4 | 5 | 6 | 7 |
| | | | | Temp, °C. | | | |
| | 166 | 160 | 173 | 175 | 181 | 180 | 184 |
| GC results | | | | | | | |
| EDA | 70.80 | 71.44 | 69.09 | 68.10 | 66.56 | 63.90 | 59.64 |
| PIP | 5.74 | 5.72 | 6.19 | 6.73 | 7.35 | 8.50 | 9.91 |
| DETA | 16.56 | 15.83 | 17.85 | 18.07 | 17.89 | 18.70 | 20.77 |
| AEP | 0.98 | 0.93 | 1.08 | 1.21 | 1.29 | 1.56 | 2.03 |
| I-TETA | 3.16 | 3.20 | 3.45 | 3.53 | 3.78 | 4.01 | 4.45 |
| PEEDA | 0.50 | 0.57 | 0.53 | 0.57 | 0.72 | 0.80 | 0.84 |
| I-TEPA | 1.02 | 1.31 | 1.10 | 1.04 | 1.38 | 1.36 | 1.25 |
| OTHER AMINES | 1.24 | 1.00 | 0.71 | 0.75 | 1.04 | 1.17 | 1.11 |
| ~EDA Conversion, % | 32.82 | 32.19 | 34.73 | 35.78 | 37.40 | 40.18 | 44.62 |
| Wt % in Product (EDA free) | | | | | | | |
| PIP | 19.65 | 20.04 | 20.04 | 21.09 | 21.98 | 23.54 | 24.55 |
| DETA | 56.74 | 55.41 | 57.74 | 56.65 | 53.48 | 51.80 | 51.47 |
| AEP | 3.36 | 3.27 | 3.49 | 3.79 | 3.85 | 4.33 | 5.04 |
| I-TETA | 10.81 | 11.19 | 11.17 | 11.07 | 11.32 | 11.10 | 11.03 |
| Other Amines | 9.43 | 10.10 | 7.57 | 7.39 | 9.38 | 9.22 | 7.92 |

Example 5

Table 4 gives the results from reacting 800 grams of EDA with 100 grams of a commercial nickel on silica catalyst at 179-180° C. and an initial hydrogen pressure of 40 psig but otherwise using the procedures of Example 2. The pressure of the reactor during the run was 650 to 1000 psig. As can be seen from the table, AEP increases with EDA conversion. Comparing these results with Table 3 which uses the same catalyst, shows these conditions at an initial lower hydrogen concentration produced more AEP at a given EDA conversion than process conditions for Table 3.

TABLE 4

Catalyst: Engelhard Ni-5256E 57% Ni on silica ⅛" extrudate

| | Run no. | | | |
|---|---|---|---|---|
| | 1 | 2 | 3 | 4 |
| | | Time, hrs | | |
| | 1 | 2 | 3 | 4 |
| | | Temp, °C. | | |
| | 179 | 180 | 180 | 180 |
| GC results | | | | |
| EDA | 64.78 | 49.98 | 38.25 | 34.26 |
| PIP | 12.21 | 18.39 | 23.26 | 24.92 |
| DETA | 13.14 | 17.03 | 19.68 | 17.99 |
| AEP | 2.64 | 4.82 | 7.04 | 7.88 |
| I-TETA | 1.92 | 2.91 | 3.68 | 3.55 |
| PEEDA | 0.86 | 1.38 | 1.88 | 2.50 |
| I-TEPA | 0.53 | 0.76 | 0.62 | 0.82 |
| OTHER AMINES | 3.92 | 4.73 | 5.60 | 8.08 |
| ~EDA Conversion, % | 38.87 | 54.05 | 65.54 | 69.20 |
| Wt % in Product (EDA free) | | | | |
| PIP | 34.67 | 36.78 | 37.67 | 37.91 |
| DETA | 37.32 | 34.04 | 31.87 | 27.36 |
| AEP | 7.50 | 9.64 | 11.40 | 11.98 |
| I-TETA | 5.46 | 5.82 | 5.96 | 5.40 |

The data in tables 1 through 4 show that converting EDA to AEP is challenging, even when using a preferred catalyst and practicing principles of the present invention. It is believed that one factor contributing to this difficulty is that much of the DETA present initially and/or formed as a reaction product is converted to PIP, making further reaction difficult. This hypothesis is borne out by the following example, where the feed includes more DETA at the outset. The example shows that starting out with a higher amine than EDA does not necessarily simplify the route to AEP.

Example 6

Table 5 gives the results from reacting 802 grams of a mixed EDA/DETA with 100 grams of a Ni/Re on alumina/silica (80:20) catalyst at 150-155° C. at an initial hydrogen pressure of 150 psig but otherwise using the procedures of Example 2. The pressure of the reactor during the run was 215 to 670 psig. As can be seen from the table, AEP increases with EDA conversion. Comparing these results with Tables 1-4 above shows this feed does not produce a significant increase in AEP in the final product mix

TABLE 5

Catalyst: Ni/Re (6.8/1.8 wt. %) on alumina/silica 80:20

| | | Run no. | | | | | | | |
|---|---|---|---|---|---|---|---|---|---|
| | | 1 | 2 | 3 | 4 | 5 | 6 | 7 | 8 |
| | | | | | Time, hrs | | | | |
| | | 1 | 2 | 3 | 4 | 5 | 6 | 7 | 8 |
| | | | | | Temp, °C. | | | | |
| | Feed | 150 | 150 | 150 | 150 | 150 | 155 | 155 | 155 |
| ~EDA Conversion, % | | 14.36 | 15.39 | 23.59 | 30.48 | 35.25 | 39.72 | 46.70 | 52.59 |
| GC results, Wt % | | | | | | | | | |
| EDA | 64.28 | 55.05 | 54.39 | 49.12 | 44.69 | 41.63 | 38.75 | 34.26 | 30.48 |
| PIP | 0.06 | 3.49 | 3.88 | 6.14 | 8.30 | 10.48 | 13.55 | 16.71 | 20.10 |

TABLE 5-continued

| Catalyst: Ni/Re (6.8/1.8 wt. %) on alumina/silica 80:20 | | | | | | | | | |
|---|---|---|---|---|---|---|---|---|---|
| | | Run no. | | | | | | | |
| | | 1 | 2 | 3 | 4 | 5 | 6 | 7 | 8 |
| | | | | | Time, hrs | | | | |
| | | 1 | 2 | 3 | 4 | 5 | 6 | 7 | 8 |
| | | | | | Temp, °C. | | | | |
| | Feed | 150 | 150 | 150 | 150 | 150 | 155 | 155 | 155 |
| DETA | 35.57 | 36.74 | 37.07 | 37.72 | 37.36 | 36.45 | 34.50 | 33.59 | 31.17 |
| AEP | 0.04 | 0.27 | 0.36 | 0.64 | 0.94 | 1.27 | 1.64 | 2.44 | 3.22 |
| I-TETA | 0.00 | 3.33 | 3.35 | 4.94 | 6.26 | 7.24 | 8.11 | 9.31 | 9.82 |
| PEEDA | 0.00 | 0.04 | 0.04 | 0.09 | 0.01 | 0.02 | 0.42 | 0.63 | 0.96 |
| I-TEPA | 0.00 | 0.60 | 0.46 | 0.87 | 1.20 | 1.39 | 1.83 | 2.06 | 2.36 |
| OTHER AMINES | 0.05 | 0.47 | 0.46 | 0.49 | 1.24 | 1.52 | 1.19 | 1.00 | 1.90 |
| total | 100.00 | 100.00 | 100.00 | 100.00 | 100.00 | 100.00 | 100.00 | 100.00 | 100.00 |

Example 2 to 5 suggests adding more DETA would give more AEP. As shown here, starting with more DETA at the outset does not lead to significantly more production of AEP. It is believed that the DETA is converted to PIP, which essentially stops further reactions as a practical matter. This shows that using even higher amines having 4 or more amines per molecule as described in further examples provides a much more effective route to cyclic amines such as AEP. It is believed that these further routes are more effective because they proceed via ring closure and/or reduction mechanisms that proceed substantially through alternative immediates rather than PIP.

Example 7

Table 6 gives the results from reacting 800 grams of a mixed ethyleneamines feed which has a large percentage of linear TETA in the mix, with 100 grams of a commercial nickel on silica catalyst at 150-155° C. in the absence of hydrogen but otherwise using the procedures of Example 2. The pressure of the reactor during the run was 286 to 730 psig. As can be seen from the table, AEP increases with feed conversion. Comparing these results with Tables 1-5 shows this feed produces a much more significant amount of AEP in the final product mix compared to when EDA or a mix of EDA/DETA is used as the feed.

TABLE 6

| Catalyst: Sud-Chemie C46-7-03, 50% Ni on silica/alumina | | | | | | | |
|---|---|---|---|---|---|---|---|
| | | Run no. | | | | | |
| | | 1 | 2 | 3 | 4 | 5 | 6 |
| | | | | Time, hrs | | | |
| | | 1 | 2 | 3 | 4 | 5 | 6 |
| | | | | Temp, °C. | | | |
| | Feed | 153 | 154 | 155 | 155 | 155 | 155 |
| ~I-TETA Conversion, % | | 28.29 | 51.22 | 68.83 | 84.34 | 92.66 | 96.80 |
| GC results, Wt % | | | | | | | |
| EDA | 0.00 | 0.99 | 1.50 | 1.86 | 1.97 | 1.82 | 1.49 |
| PIP | 0.00 | 1.63 | 2.76 | 4.25 | 6.07 | 7.39 | 8.36 |
| DETA | 0.06 | 1.50 | 1.64 | 1.67 | 1.35 | 0.96 | 0.09 |
| AEP | 0.64 | 13.11 | 24.11 | 31.89 | 38.60 | 41.85 | 43.06 |
| I-TETA | 80.97 | 58.06 | 39.49 | 25.24 | 12.68 | 5.94 | 2.59 |
| PEEDA | 3.70 | 6.28 | 8.71 | 10.94 | 13.58 | 15.46 | 16.68 |
| I-TEPA | 8.02 | 7.36 | 6.23 | 5.09 | 3.52 | 2.29 | 1.44 |
| OTHER AMINES | 6.61 | 11.07 | 15.54 | 19.06 | 22.23 | 24.29 | 26.30 |
| total | 100.00 | 100.00 | 100.00 | 100.00 | 100.00 | 100.00 | 100.00 |

Example 8

This example uses a commercially available TETA obtained from an EDC process. Table 7 shows the composition of the commercial product and gives the results from reacting 800 grams of the mixed ethyleneamines feed, which has a large percentage of linear TETA in the mix, with 100 grams of a commercial nickel on silica catalyst at 150° C. and an initial hydrogen pressure of 36 psig but otherwise using the procedures of Example 2. The pressure of the reactor during the run was 186 to 613 psig. As can be seen from the table, AEP increases with feed conversion. Comparing these results with Tables 1-5 shows this feed produces a much more significant amount of AEP in the final product mix compared to when EDA or EDA/DETA is used as the feed. However, it produces a lower amount of AEP in the final product mix than the process in Table 6 due to the lower amount of linear TETA in the feed.

TABLE 7

Catalyst: Sud-Chemie C46-7-03, 50% Ni on silica/alumina

| | | Run no. | | | | |
|---|---|---|---|---|---|---|
| | | 1 | 2 | 4 | 5 | 6 |
| | | | | Time, hrs | | |
| | | 1 | 2 | 4 | 5 | 6 |
| | | | | Temp, °C. | | |
| | Feed | 150 | 150 | 150 | 150 | 150 |
| ~l-TETA Conversion, % | | 43.52 | 64.52 | 78.14 | 88.92 | 95.57 |
| GC results, Wt % | | | | | | |
| EDA | 0.05 | 1.03 | 1.54 | 1.74 | 1.51 | 1.25 |
| PIP | 0.01 | 1.84 | 3.64 | 4.96 | 5.38 | 6.30 |
| DETA | 0.14 | 1.41 | 1.69 | 1.53 | 1.09 | 0.64 |
| AEP | 0.02 | 12.59 | 22.48 | 28.15 | 28.27 | 29.51 |
| TAEA | 4.48 | 1.75 | 0.74 | 0.32 | 0.11 | 0.03 |
| I-TETA | 59.61 | 33.67 | 21.15 | 13.03 | 6.61 | 2.64 |
| DAEP | 12.63 | 12.20 | 12.57 | 12.42 | 10.65 | 9.66 |
| PEEDA | 20.48 | 20.63 | 22.58 | 23.58 | 21.30 | 20.60 |
| I-TEPA | 0.02 | 1.79 | 2.20 | 2.04 | 1.47 | 0.96 |
| OTHER AMINES | 2.56 | 13.10 | 11.40 | 12.22 | 23.61 | 28.41 |
| total | 100.00 | 100.00 | 100.00 | 100.00 | 100.00 | 100.00 |

Example 9

Table 8 gives the results from reacting 800 grams of TAEA, with 100 grams of a commercial nickel on silica catalyst at 150° C. in the absence of hydrogen but otherwise using the procedures of Example 2. The pressure of the reactor during the run was 213 to 730 psig. As can be seen from the table, AEP increases with TAEA conversion. Comparing these results with Tables 1-7 show that TAEA produces significantly more AEP in the final product mix compared to when EDA, EDA/DETA, or feeds which have a high percentage of linear TETA is used as the feed.

TABLE 8

Catalyst: Sud-Chemie C46-7-03, 50% Ni on silica/alumina

| | | Run no. | | | | |
|---|---|---|---|---|---|---|
| | | 1 | 2 | 3 | 4 | 5 |
| | | | | Time, hrs | | |
| | | 1 | 2 | 3 | 4 | 5 |
| | | | | Temp, °C. | | |
| | Feed | 150 | 150 | 150 | 150 | 150 |
| ~TAEA Conversion, % | | 34.99 | 58.52 | 76.69 | 90.59 | 97.20 |
| GC results, Wt % | | | | | | |
| EDA | 0.00 | 0.04 | 0.06 | 0.13 | 0.13 | 0.13 |
| PIP | 0.00 | 0.24 | 0.50 | 0.87 | 1.22 | 1.55 |
| DETA | 0.12 | 0.67 | 0.73 | 0.67 | 0.42 | 0.21 |
| AEP | 0.01 | 30.49 | 47.66 | 64.01 | 71.38 | 74.91 |
| TAEA | 97.11 | 63.13 | 40.28 | 22.64 | 9.14 | 2.72 |
| I-TETA | 0.01 | 0.02 | 0.02 | 0.04 | 0.27 | 0.35 |
| DAEP | 0.03 | 0.00 | 0.00 | 0.01 | 0.00 | 0.00 |
| PEEDA | 0.03 | 0.10 | 0.23 | 0.46 | 0.74 | 1.09 |
| I-TEPA | 0.13 | 0.07 | 0.04 | 0.02 | 0.01 | 0.01 |
| OTHER AMINES | 2.54 | 5.23 | 10.48 | 11.17 | 16.67 | 19.04 |
| total | 100.00 | 100.00 | 100.00 | 100.00 | 100.00 | 100.00 |

Example 10

Table 9 gives the results from reacting 147 grams of TEA and 189 grams of ammonia with 50 grams of a Ni/Re on alumina/silica (80:20) catalyst at 160-170° C. and an initial hydrogen pressure of 450 psig. The pressure of the reactor during the run was 1644 to 1910 psig. As can be seen from the table, AEP increases with TEA conversion. Comparing these results with Tables 1-5 shows that TEA produces significantly more AEP in the final product mix compared to when EDA or EDA/DETA is used as the feed.

TABLE 9

Catalyst: Ni/Re (6.8/1.8 wt. %) on alumina/silica 80:20

| | | Run no. | | | | | | | |
|---|---|---|---|---|---|---|---|---|---|
| | | 1 | 2 | 3 | 4 | 5 | 6 | 7 | 8 | 9 |
| | | | | | | Time, hrs | | | | |
| | | 1 | 2 | 3 | 4 | 5 | 10 | 12 | 14 | 16 |
| | | | | | | Temp, °C. | | | | |
| | Feed | 160 | 160 | 164 | 165 | 170 | 170 | 170 | 170 | 170 |
| ~TEA Conversion, % GC results, Wt % | | 22.23 | 34.28 | 50.92 | 59.57 | 70.58 | 92.03 | 96.70 | 98.60 | 99.62 |
| EDA | 0.00 | 2.00 | 2.24 | 2.12 | 2.05 | 1.86 | 1.64 | 1.59 | 1.56 | 1.51 |
| Piperazine | 0.01 | 0.26 | 0.55 | 1.23 | 1.85 | 3.00 | 7.50 | 9.65 | 11.14 | 12.41 |
| DETA | 0.00 | 0.02 | 0.07 | 0.00 | 0.13 | 0.11 | 0.00 | 0.15 | 0.00 | 0.17 |
| AEEA | 0.00 | 0.05 | 0.15 | 0.32 | 0.42 | 0.18 | 0.03 | 0.18 | 0.11 | 0.06 |

TABLE 9-continued

| Catalyst: Ni/Re (6.8/1.8 wt. %) on alumina/silica 80:20 | | | | | | | | | |
|---|---|---|---|---|---|---|---|---|---|
| | Run no. | | | | | | | | |
| | 1 | 2 | 3 | 4 | 5 | 6 | 7 | 8 | 9 |
| | Time, hrs | | | | | | | | |
| | 1 | 2 | 3 | 4 | 5 | 10 | 12 | 14 | 16 |
| | Temp, ° C. | | | | | | | | |
| Feed | 160 | 160 | 164 | 165 | 170 | 170 | 170 | 170 | 170 |
| AEP | 0.03 | 0.30 | 0.60 | 1.04 | 2.17 | 5.07 | 20.57 | 30.63 | 37.48 | 42.30 |
| HEP | 0.00 | 2.69 | 5.75 | 12.84 | 18.52 | 26.31 | 38.29 | 34.63 | 27.44 | 19.51 |
| DIHEED (unsymmetrical) | 0.01 | 15.08 | 23.28 | 28.61 | 29.69 | 27.86 | 11.44 | 5.35 | 2.30 | 0.79 |
| TEA | 99.27 | 77.20 | 65.24 | 48.72 | 40.14 | 29.20 | 7.91 | 3.27 | 1.39 | 0.37 |
| Other amines | 0.67 | 2.39 | 2.11 | 5.11 | 5.03 | 6.40 | 12.62 | 14.56 | 18.58 | 22.87 |
| Total | 100.00 | 100.00 | 100.00 | 100.00 | 100.00 | 100.00 | 100.00 | 100.00 | 100.00 | 100.00 |

Example 11

Table 10 gives the results from reacting 254 grams of HEP and 292 grams of ammonia with 50 grams of a Ni/Re on alumina/silica (80:20) catalyst at 160-170° C. and an initial hydrogen pressure of 500 psig but otherwise using the procedures of Example 2. The pressure of the reactor during the run was 2000 to 2290 psig. As can be seen from the table, AEP increases with HEP conversion, up to ca. 85 percent, after which AEP is consumed faster than its make rate. Comparing these results with Tables 1-5 shows that HEP produces significantly more AEP in the final product mix compared to when EDA or EDA/DETA is used as the feed.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of making a cyclic triamine of the type comprising first and second nitrogen backbone atoms and an N-amino moiety pendant from at least one of the nitrogen backbone atoms, comprising the steps of:

TABLE 10

| Catalyst: Ni/Re (6.8/1.8 wt. %) on alumina/silica 80:20 | | | | | | | | | | |
|---|---|---|---|---|---|---|---|---|---|---|
| | Run no. | | | | | | | | | |
| | 1 | 2 | 3 | 4 | 5 | 6 | 7 | 8 | 9 | 10 |
| | Time, hrs | | | | | | | | | |
| | 2 | 4 | 6 | 9 | 11 | 13 | 15 | 17 | 19 | 21 |
| | Temp, ° C. | | | | | | | | | |
| Feed | 165 | 165 | 170 | 175 | 175 | 175 | 175 | 180 | 180 | 180 |
| ~HEP Conversion, % | | 0.59 | 2.84 | 7.88 | 35.37 | 45.41 | 56.76 | 65.23 | 78.30 | 86.88 | 92.76 |
| GC results, Wt % | | | | | | | | | | |
| EDA | 0.00 | 0.01 | 0.02 | 0.07 | 0.35 | 0.45 | 0.55 | 0.64 | 0.64 | 0.77 | 0.90 |
| Piperazine | 0.00 | 0.10 | 0.13 | 0.31 | 1.64 | 2.27 | 3.15 | 3.96 | 5.12 | 6.68 | 8.10 |
| AEP | 0.00 | 1.01 | 3.20 | 7.71 | 31.13 | 38.89 | 46.85 | 51.92 | 57.65 | 57.96 | 55.23 |
| HEP | 94.89 | 94.33 | 92.19 | 87.42 | 61.33 | 51.80 | 41.03 | 33.00 | 20.59 | 12.45 | 6.87 |
| PEEDA | 0.00 | 0.01 | 0.00 | 0.01 | 0.28 | 0.58 | 1.06 | 1.62 | 2.70 | 3.68 | 4.55 |
| L-TEPA | 0.05 | 0.01 | 0.01 | 0.01 | 0.00 | 0.00 | 0.00 | 0.00 | 0.00 | 0.00 | 0.01 |
| BPEA | 0.01 | 0.00 | 0.00 | 0.02 | 0.55 | 1.00 | 1.81 | 2.67 | 4.67 | 6.59 | 8.76 |
| Other amines | 5.05 | 4.53 | 4.44 | 4.46 | 4.72 | 5.00 | 5.54 | 6.19 | 8.64 | 11.87 | 15.58 |
| Total | 100.00 | 100.00 | 100.00 | 100.00 | 100.00 | 100.00 | 100.00 | 100.00 | 100.00 | 100.00 | 100.00 | providing a polyfunctional compound comprising at least 4 amine moieties and, optionally, one or more nitrile moieties said polyfunctional compound being selected from the group a)

TAEA b) one or more tetramines; and
c) a polyamine having at least one nitrile moiety; and
causing ring closure of the polyfunctional compound in the presence of a transamination catalyst under conditions effective to cause the polyfunctional compound to react with itself to form the cyclic triamine.

2. The method of claim 1, wherein the polyfunctional compound comprises one or more tetraamines.

3. The method of claim 1, wherein the polyfunctional compound is

TAEA

4. The method of claim 1, wherein the polyfunctional compound comprises a polyamine having at least one nitrile moiety.

5. The method of claim 1, wherein the catalyst comprises Ni and Re.

* * * * *